(12) United States Patent
Yang et al.

(10) Patent No.: US 9,851,315 B2
(45) Date of Patent: Dec. 26, 2017

(54) METHODS FOR QUANTITATIVE CHARACTERIZATION OF ASPHALTENES IN SOLUTIONS USING TWO-DIMENSIONAL LOW-FIELD NMR MEASUREMENT

(71) Applicants: Zheng Yang, Hercules, CA (US); Boqin Sun, Houston, TX (US); Ajit Ramchandra Pradhan, Walnut Creek, CA (US); Hussein Alboudwarej, San Ramon, CA (US); Dengen Zhou, Sugarland, TX (US)

(72) Inventors: Zheng Yang, Hercules, CA (US); Boqin Sun, Houston, TX (US); Ajit Ramchandra Pradhan, Walnut Creek, CA (US); Hussein Alboudwarej, San Ramon, CA (US); Dengen Zhou, Sugarland, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 490 days.

(21) Appl. No.: 14/567,364

(22) Filed: Dec. 11, 2014

(65) Prior Publication Data

US 2016/0169820 A1    Jun. 16, 2016

(51) Int. Cl.
*G01N 24/08*  (2006.01)
*G01N 33/24*  (2006.01)
(Continued)

(52) U.S. Cl.
CPC ......... *G01N 24/081* (2013.01); *G01N 33/241* (2013.01); *G01R 33/448* (2013.01); *G01V 3/32* (2013.01); *G01R 33/445* (2013.01)

(58) Field of Classification Search
CPC .............................. G06F 19/70; G01N 24/081
See application file for complete search history.

(56) References Cited

U.S. PATENT DOCUMENTS 4,710,713 A   12/1987  Strikman
4,717,876 A    1/1988  Masi et al.
(Continued)

FOREIGN PATENT DOCUMENTS

CN    102062742    5/2011
DE    2121799 C2   7/1982
(Continued)

OTHER PUBLICATIONS

Wang, Jianxin et al. "Asphaltene stability in crude oil and aromatic solvents—the influence of oil composition." Energy and Fuels (2003) 17 1445-1451.*

(Continued)

*Primary Examiner* — Christopher Adam Hixson
(74) *Attorney, Agent, or Firm* — Susan M. Abernathy (57) ABSTRACT

A method for determining the concentration of asphaltenes in a solution is described. A model is first established for estimating the concentration of asphaltenes in a solution based on multiple samples of solutions of asphaltenes in the solvent in which the concentrations are known. The multiple samples have varying concentrations of asphaltenes. The diffusivity and relaxation time are measured for each sample using two-dimensional NMR. The ratio of diffusivity to relaxation time for each sample is then calculated. A linear equation is determined to fit the relationship between the ratio of diffusivity to relaxation time and the asphaltene concentration by weight for the multiple samples, thus creating the model. For a given solution sample for which the concentration of asphaltenes is desired to be determined, diffusivity and relaxation time are determined using two-dimensional NMR, and the ratio of diffusivity to relaxation time is calculated. This ratio is then used with the model, so that the linear equation can be solved for the asphaltene concentration in the given solution sample.

14 Claims, 4 Drawing Sheets

(51) Int. Cl.
  *G01V 3/32* (2006.01)
  *G01R 33/50* (2006.01)
  *G01R 33/44* (2006.01)

(56) References Cited

U.S. PATENT DOCUMENTS

| | | |
|---|---|---|
| 4,717,877 A | 1/1988 | Taicher et al. |
| 4,717,878 A | 1/1988 | Taicher et al. |
| 4,827,761 A | 5/1989 | Vinegar et al. |
| 5,023,551 A | 6/1991 | Kleinberg et al. |
| 5,055,787 A | 10/1991 | Kleinberg et al. |
| 5,055,788 A | 10/1991 | Kleinberg et al. |
| 5,200,699 A | 5/1993 | Baldwin et al. |
| 5,212,447 A | 5/1993 | Paltiel |
| 5,280,243 A | 1/1994 | Miller |
| 5,291,137 A | 3/1994 | Freedman |
| 5,309,098 A | 5/1994 | Coates et al. |
| 5,363,041 A | 11/1994 | Sezginer |
| 5,381,092 A | 1/1995 | Freedman |
| 5,412,320 A | 5/1995 | Coates |
| 5,459,677 A * | 10/1995 | Kowalski ............. G01N 21/274 250/252.1 |
| 5,486,762 A | 1/1996 | Freedman et al. |
| 5,517,115 A | 5/1996 | Prammer |
| 5,557,200 A | 9/1996 | Coates |
| 5,585,720 A | 12/1996 | Edwards |
| 5,680,043 A | 10/1997 | Hurlimann et al. |
| 5,696,448 A | 12/1997 | Coates et al. |
| 5,796,252 A | 8/1998 | Kleinberg et al. |
| 5,936,405 A | 8/1999 | Prammer et al. |
| 6,005,389 A | 12/1999 | Prammer |
| 6,032,101 A | 2/2000 | Freedman et al. |
| 6,049,205 A | 4/2000 | Taicher et al. |
| 6,069,477 A | 5/2000 | Chen et al. |
| 6,070,662 A | 6/2000 | Ciglenec et al. |
| 6,072,314 A | 6/2000 | Oraby |
| 6,114,851 A | 9/2000 | Kruspe et al. |
| 6,133,735 A | 10/2000 | Hurlimann et al. |
| 6,147,489 A | 11/2000 | Freedman et al. |
| 6,166,543 A | 12/2000 | Sezginer et al. |
| 6,255,818 B1 | 7/2001 | Heaton et al. |
| 6,316,940 B1 | 11/2001 | Akkurt |
| 6,344,744 B2 | 2/2002 | Taicher et al. |
| 6,366,087 B1 | 4/2002 | Coates et al. |
| 6,369,567 B1 | 4/2002 | Song et al. |
| 6,429,653 B1 | 8/2002 | Kruspe et al. |
| 6,462,542 B1 | 10/2002 | Venkataramanan et al. |
| 6,477,516 B1 | 11/2002 | Colaiocco et al. |
| 6,492,809 B1 | 12/2002 | Speier et al. |
| 6,522,136 B1 | 2/2003 | Hurlimann et al. |
| 6,559,639 B2 | 5/2003 | Minh et al. |
| 6,559,640 B2 | 5/2003 | Taicher |
| 6,570,382 B1 | 5/2003 | Hurlimann et al. |
| 6,573,715 B2 | 6/2003 | King et al. |
| 6,577,125 B2 | 6/2003 | Prammer et al. |
| 6,583,621 B2 | 6/2003 | Prammer et al. |
| 6,597,171 B2 | 7/2003 | Hurlimann et al. |
| 6,745,833 B2 | 6/2004 | Aronstam et al. |
| 6,833,699 B2 | 12/2004 | Galford et al. |
| 6,937,014 B2 | 8/2005 | Sun |
| 6,959,246 B2 | 10/2005 | Herron |
| 6,977,499 B2 | 12/2005 | Kiesl et al. |
| 6,984,980 B2 | 1/2006 | Kruspe et al. |
| 7,193,414 B2 | 3/2007 | Kruspe et al. |
| 7,398,837 B2 | 7/2008 | Hall et al. |
| 7,452,930 B2 | 11/2008 | Kawakami et al. |
| 7,605,716 B2 | 10/2009 | Peter et al. |
| 7,624,794 B2 | 12/2009 | Freedman et al. |
| 7,683,613 B2 | 3/2010 | Freedman et al. |
| 7,733,086 B2 | 6/2010 | Prammer et al. |
| 7,755,354 B2 | 7/2010 | Akkurt |
| 7,893,692 B2 | 2/2011 | Minh |
| 8,016,036 B2 | 9/2011 | Kirkwood et al. |
| 2002/0067164 A1 | 6/2002 | Venkataramanan et al. |
| 2002/0105326 A1 | 8/2002 | Hurlimann et al. |
| 2003/0094946 A1 | 5/2003 | Galford et al. |
| 2003/0155915 A1 | 8/2003 | Kruspe et al. |
| 2004/0169511 A1 | 9/2004 | Minh et al. |
| 2004/0189296 A1 | 9/2004 | Sun et al. |
| 2005/0030021 A1 | 2/2005 | Prammer et al. |
| 2009/0157350 A1 | 6/2009 | Salazar et al. |
| 2009/0256562 A1 | 10/2009 | Gao et al. |
| 2009/0302847 A1 | 12/2009 | Knizhnik |
| 2010/0156409 A1 | 6/2010 | Nikolin et al. |
| 2011/0050223 A1 | 3/2011 | Balcom et al. |
| 2011/0198078 A1 | 8/2011 | Harrigan et al. |
| 2011/0284231 A1 | 11/2011 | Becker |
| 2012/0092016 A1 | 4/2012 | Kruspe |
| 2012/0169334 A1 * | 7/2012 | Hopper ................ G01N 24/081 324/303 |
| 2012/0192640 A1 | 8/2012 | Minh et al. |
| 2012/0223235 A1 | 9/2012 | Maucec |
| 2013/0103627 A1 | 4/2013 | Maddinelli et al. |
| 2013/0293228 A1 | 11/2013 | Walsh et al. |
| 2014/0035574 A1 | 2/2014 | Wang et al. |
| 2014/0088878 A1 | 3/2014 | Chen et al. |
| 2014/0229112 A1 | 8/2014 | Datey et al. |
| 2014/0232391 A1 | 8/2014 | Viswanathan |
| 2014/0320126 A1 | 10/2014 | Heaton et al. |
| 2014/0340082 A1 | 11/2014 | Yang et al. |
| 2015/0268323 A1 * | 9/2015 | Song ..................... G01V 3/32 324/303 |

FOREIGN PATENT DOCUMENTS

| | | |
|---|---|---|
| EP | 1397661 B1 | 9/2008 |
| EP | 2584381 | 4/2013 |
| GB | 2489005 | 9/2012 |
| JP | 03167291 A | 7/1991 |
| WO | 1999/045234 | 9/1999 |
| WO | 01/42817 A1 | 6/2001 |
| WO | 2007106810 | 9/2007 |
| WO | 2008082325 | 7/2008 |
| WO | 2011/014456 A1 | 2/2011 |
| WO | 2011/133859 | 10/2011 |
| WO | 2012/068219 | 5/2012 |
| WO | 2013/023011 | 2/2013 |
| WO | 2013/148516 | 10/2013 |
| WO | 2013/184404 | 12/2013 |

OTHER PUBLICATIONS

Martinez et al., "Lanosterol and cholesterol-indueced variations in Bilayer elasticity probed by H NMR relaxation," Langmuir, (2003).
Mohnke O Et Al. "Smooth and block inversion of surface NMR amplitudes and decay times using simulated annealing" Journal of Applied Geophysics—Surface Nuclear Magnetic Resonance, May 2002 Elsevier NL, vol. 50, No. 1-2, May 2002.
Sun et al., "Methods and limitations of NMR data inversion for fluid typing," Journal of Magnetic Resonance, 169 (2004).
Brunger et al., "New applications of simulated annealing in X-ray crystallography and solution NMR," Structure, 1997, vol. 5, No. 3, p. 325-336.
Sun et al: "In situ fluid typing and quantification with 1D 2D NMR logging" Magnetic Resonance Imaging, Tarrytown, NY, US, vol. 25, No. 4, May 4, 2007 ( May 4, 2007) pp. 521-524.
Song et al: "Novel NMR techniques for porous media research" Cement and Concrete Research, Pergamon Press, Elmsford, NY, US, vol. 37, No. 3, Feb. 22, 2007 (Feb. 22, 2007), pp. 325-328.
Parker R L et al: "Assigning uncertainties in the inversion of NMR relaxation data" Journal of Magnetic Resonance, Academic Press, Orlando, FL, US, vol. 174, No. 2, Jun. 1, 2005 (Jun. 1, 2005), pp. 314-324.
Press W.H.: "Numerical Recipes in C" 1995, Cambridge University Press, Cambridge, pp. 394-397, p. 444-p. 445.
Arns C H et al: "Multidimensional NMR inverse laplace spectroscopy in petrophysics" Petrophysics Oct. 2007 Society of Well Log Analysts Inc. US, vol. 48, No. 5, Oct. 2007 (Oct. 2007), pp. 380-392.
K. Binder, The Monte Carlo Method in Condensed Matter Physics, Topics in Applied Physics, vol. 71 Springer-Verlag, Berlin, 1992, 22 pages.

(56) References Cited

OTHER PUBLICATIONS

Sun et al., A global inversion method for multi-dimensional NMR logging, Journal of Magnetic Resonance, vol. 172, 2005, pp. 152-160.

Miller et al., "A New Method for Estimating T2 Distributions from NMR Measurements", Magnetic Resonance Imaging, vol. 16, Nos. 5/6, 1998, pp. 617-619.

Salazar et al., "Simulated Annealing Using Hybrid Monte Carlo", Journal of Statistical Physics, vol. 89, Nos. 5/6, 1997, pp. 1047-1060.

English, A.E., Whittall, K.P., Joy, M.L.G., and Henkelman, R.M., Quantitative Two-Dimensional Time Correlation Relaxometry, Magnetic Resonance in Medicine, 22, 425-434, 1991.

Lee, J-H., Labadie, C., Springer, C. S., and Harbison, G. S., Two-Dimensional Inverse Laplace Transform NMR: Altered Relaxation Times Allow Detection of Exchange Correlation, J. Am. Chem. Soc., 115, 7761-7764, 1993.

Akkurt, R., Vinegar, H. J., Tutunjian, P.N., and Guillory, A.J., NMR Logging of Natural Gas Reservoirs, The Log Analyst, 33-42, Nov.-Dec. 1996.

Dunn, K-J. and Latorraca, G.A., The Inversion of NMR Log Data Sets with Different Measurement Errors, Journal of Magnetic Resonance, 140, 153-161, 1999.

Chen, S., Georgi, D.T., Withjack, E.M., Minetto, C., Olima, O., and Gamin, H., Estimation of Oil Viscosity with Multiple TE Dual Wait-Time MRIL Logs, Petrophysics, vol. 41, No. 1, 33-39, Jan.-Feb. 2000.

Freedman, R., Sezginer, A., Flaum, M., Matteson, A., Lo, S., and Hirasaki, G.J., A New NMR Method of Fluid Characterization in Reservoir Rocks: Experimental Confirmation and Simulation Results, Society of Petroleum Engineers (SPE Paper 63214), 1-15, 2000.

Dunn, K-J., Appel, M., Freeman, J.J., Gardner, J. S., Hirasaki, G.J., Shafer, J.L., and Zhang, G., Interpretation of Restricted Diffusion and Internal Field Gradients in Rock Data, Published in the Proceedings of $42^{nd}$ Annual Symposium of Society of Professional Well Log Analysts, Houston, TX, Paper AAA, 1-12, 2001.

Venkataramanan, L., Song, Y-Q., and Hürlimann, M.D., Solving Fredholm Integrals of the First Kind with Tensor Product Structure in 2 and 2.5 Dimensions, IEEE Transactions on Signal Processing, vol. 50, No. 5, 1017-1026, May 2002.

Hürlimann, M.D., Venkataramanan, L., Flaum, C., Speier, P., Karmonik, C., Freedman, R., and Heaton, N., Diffusion-Editing: New NMR Measurement of Saturation and Pore Geometry, SPWLA $43^{rd}$ Annual Logging Symposium, Paper FFF, 1-14, Jun. 2-5, 2002.

Dunn, K-J., Enhanced Transverse Relaxation in Porous Media Due to Internal Field Gradients, Journal of Magnetic Resonance 156, 1-10, 2002.

Hürlimann, M.D., and Venkataramanan, L., Quantitative Measurement of Two-Dimensional Distribution Functions of Diffusion and Relaxation in Grossly Inhomogeneous Fields, Journal of Magnetic Resonance 157, 31-42, 2002.

Sun, B. and Dunn, K-J., Probing the Internal Field Gradients of Porous Media, The American Physical Society, Physical Review E, vol. 65, 051309, 1-7, 2002.

Godefroy, S., et al.; "Temperature Effect on NMR Surface Relaxation in Rocks for Well Logging Applications"; J. Phys. Chem. B. 2002, vol. 106,pp. 11183-11190, XP-002729750.

Han, H., et al.; "High Pressure Magnetic Resonance Imaging with Metallic Vessels"; Journal of Magnetic Resonance, 2011, vol. 213, DD. 90-97.

Anderson, Robert J., et al.; "NMR Methods of Characterizing the Pore Structures and Hydrogen Storage Properties of Microporous Carbons"; J. Am. Chem. Soc., 2010, vol. 132, pp. 8618-8626.

Kausik, Ravinath, et al.; "Characterization of Gas Dynamics in Kerogen Nanopores by NMR"; Oct.-Nov. 2011, SPE 147198, pp. 1-16.

Mitchell, J., et al.; "Nuclear Magnetic Resonance Cryoporometry"; 2008, Physics Reports, vol. 461, pp. 1-36.

Musharfi, Nedhal, et al.; "Combining Wireline Geochemical, NMR, and Dielectric Data for Formation Evaluation and Characterization of Shale Reservoirs"; SPWLA 53rct Annual Logging Symposium, Jun. 2012, pp. 1-16.

Peterson, Ronald W., et al.; "Self Contained High Pressure Cell, Apparatus and Procedure for the Preparation of Encapsulated Proteins Dissolved in Low Viscosity Fluids for NMR Spectroscopy"; Sep. 2005, Rev. Sci. Instmm., 76(9); pp. 1-7.

Song, Y.-Q., et al.; "$T_1$-$T_2$ Correlation Spectra Obtained Using a Fast Two-Dimensional Laplace Inversion"; 2002, Journal of Magnetic Resonance, vol. 154, DD. 261-268.

Sun, Boqin, et al.; "A Global Inversion Method for Multi-Dimensional NMR Logging"; 2005, Journal of Magnetic Resonance, vol. 172,pp, 152-160.

Sun, Boqin, et al.; "Core Analysis with Two Dimensional NMR"; SCA2002-38, pp. 1-12.

Sun, Boqin, et al.; "NMR Inversion Methods for Fluid Typing"; SPWLA 44tn Annual Logging Symposium, Jun. 2003, pp. 1-12.

Sun, Boqin, et al.; "NMR Isotherm Studies of Gas Shales"; SPWLA 57tn Annual Logging Symposium, Jun. 2016, DD. 1-14.

Wang, Hai-Jing, et al.; "High-Field Nuclear Magnetic Resonance Observation of Gas Shale Fracturing by Methane Gas"; Energy & Fuels, 2014, vol. 28, DD. 3638-3644.

Wang, Hai-Jing, et al.; "Water Adsorption in Nanoporous Carbon Characterized by in Situ NMR: Measurements of Pore Size and Pore Size Distribution"; 2014, The Journal of Physical Chemistry C, vol. 118, DD. 8474-8480.

Mitchell, J. et al. "Magnetic Resonance Imaging in Laboratory Petrophysical Core Analysis", Physics Reports, 2014, vol. 526, pp. 165-225.

\* cited by examiner

METHODS FOR QUANTITATIVE CHARACTERIZATION OF ASPHALTENES IN SOLUTIONS USING TWO-DIMENSIONAL LOW-FIELD NMR MEASUREMENT

FIELD

The present invention relates to determining the concentration of asphaltenes in solutions using two-dimensional low field NMR measurement. The present invention further relates to NMR logging and analysis of subterranean formations.

BACKGROUND

Asphaltenes can be defined as the fraction of petroleum that is soluble in aromatics such as toluene and benzene and insoluble in paraffins such as hexane, heptane and decane. Better understanding of asphaltene concentration distributions in reservoirs would be helpful because of the huge dependence of crude oil viscosity on asphaltene content and the difficulties asphaltenes can present. Asphaltene precipitation and deposition in the oil field, which directly relate to asphaltene content in a hydrocarbon reservoir, are notorious for clogging subsurface formations, wells, flowlines, and surface facilities and can cause enormous disruption in oil production.

The current existing methods for in-situ measuring asphaltene content in producing reservoirs include downhole fluid analysis (DFA) in which measurements are made using optical filters that provide for identification of the color of the fluid in the reservoir. However, DFA focuses on the compositional analysis and is therefore of limited utility in determining the concentration distribution of asphaltenes.

Low-field NMR has been applied widely to well logging and the study of hydrocarbon samples in the petroleum industry. One-dimensional NMR (1D NMR), which usually measures transverse relaxation time, also referred to as spin-spin relaxation time, transverse relaxation time or T2, is limited in identification and quantitative evaluation of reservoir fluid components since the signals from different reservoir fluid components coexisting in local pores sometimes overlap each other in the T2 spectrum. This is particularly common in heavy oil reservoirs.

Improved in-situ quantification of asphaltene content in crude oils would be of significant benefit to the industry.

SUMMARY

In one aspect, a method for determining the concentration of asphaltenes in a solution is provided. First, a model is established for estimating the concentration of asphaltenes in a solution. The model is established by preparing multiple samples of solutions of asphaltenes in a solvent. The multiple samples have varying concentrations of asphaltenes and the asphaltene concentration is known for each sample. The diffusivity and relaxation time are measured for each sample using two-dimensional NMR. The ratio of diffusivity to relaxation time for each sample is then calculated. A linear equation is determined to fit the relationship between the ratio of diffusivity to relaxation time and the asphaltene concentration by weight for the multiple samples, thus creating the model. For a given solution sample for which the concentration of asphaltenes is desired to be determined, diffusivity and relaxation time are determined using two-dimensional NMR, and the ratio of diffusivity to relaxation time is calculated. This ratio is then used with the model, so that the linear equation can be solved for the asphaltene concentration in the given solution sample.

In another aspect, a system is provided for determining the concentration of asphaltenes in a solution. The system includes an NMR probe located in contact with a fluid solution for determining diffusivity and relaxation time of the fluid solution. The system further includes a computer processor for receiving the diffusivity and relaxation time of the fluid solution from the NMR probe. The computer processor is capable of calculating the ratio of diffusivity to relaxation time for the fluid solution, accessing a linear equation describing the relationship between the ratio of diffusivity to relaxation time and the asphaltene concentration by weight, and solving the linear equation to determine the asphaltene concentration by weight in the fluid solution using the ratio of diffusivity to relaxation time for the fluid solution.

DESCRIPTION OF THE DRAWINGS

These and other objects, features and advantages of the present invention will become better understood with reference to the following description, appended claims and accompanying drawings where:

DETAILED DESCRIPTION

NMR is a known test method for obtaining information about a sample of a substance. Test measurements involve generating a magnetic field within a sample, emitting electromagnetic pulses, also referred to as RF pulses, into the sample, and detecting NMR responses from the sample. NMR has been used to characterize many properties of fluids in the hydrocarbon reservoirs. One of the NMR measured parameters is spin-lattice relaxation time, also referred to as T1. This refers to the time it takes for an assembly of magnetic moments to align along the direction of a magnetic is applied. Another related and frequently used NMR measured parameter is the spin-spin relaxation time T2, also referred to as transverse relaxation time, which is a relaxation time related to non-homogeneities in the local magnetic field in the test sample.

In low-frequency two-dimensional nuclear magnetic resonance spectroscopy, also referred to as low frequency two-dimensional NMR and low-frequency 2-D NMR, the measurement of two-dimensional distribution functions between two dissipative quantities, such as relaxation and diffusion, is based on sequences where two or more independent times are varied in such a way that the kernel separates out. These experiments are analogous to conventional multidimensional NMR spectroscopy, where the kernels are typically phase factors of an exponential form and the distribution function is obtained from the measured magnetization by multidimensional Fourier transformation. By contrast, in low-frequency 2-D NMR, the kernels for relaxation and diffusion measurements are generally of an exponential form, and the data inversion requires a multidimensional inverse Laplace transformation.

In one embodiment, two-dimensional NMR is used in a method for determining the concentration of asphaltenes in a solution. First, multiple samples of solutions of asphaltenes in a solvent are prepared. In one embodiment, the solvent is toluene. Each of the multiple samples has a different concentration of asphaltenes in toluene. For each of the samples, the concentration of the sample is known. The diffusivity, also referred to as the diffusion coefficient and D, is measured for each sample using NMR. Transverse Relaxation time also referred to as T2, is also measured for each sample using NMR. The ratio of diffusivity to T2 for each sample can then be calculated. A linear equation can then be fitted to a plot of the ratio of diffusivity to T2 and the asphaltene concentration by weight for the multiple samples. The resulting linear equation is the model for estimating the concentration of asphaltenes in a solution.

The model determined as described above can then be used to determine the concentration of asphaltenes for a given solution sample for which the concentration of asphaltenes is unknown and desired to be determined. For the given solution sample, diffusivity and T2 are determined using NMR. The ratio of diffusivity to T2 is calculated. The model is then solved for the asphaltene concentration in the given solution sample.

In one embodiment, a system is provided for performing the above-described method. The system includes an NMR probe, a transmitter capable of generating RF pulses to be emitted by the probe, and a receiver capable of being tuned to detect and amplify signals received in the NMR probe. The probe is connected to the transmitter and the receiver. The system also includes a processor for processing the signals detected and amplified by the receiver. The processor is connected to the receiver.

The probe includes one or more RF coils tuned to the proper frequencies for the substances being measured in a given magnetic field and the proper impedance. The coils both emit the pulses and detect NMR signals. The probe also includes a network of capacitors. The RF coils and network of capacitors the couple the probe circuit. The probe can also include the necessary hardware to control the sample temperature.

The NMR probe is located proximate a given solution sample for which the concentration of asphaltenes is desired to be determined. In some embodiments, the NMR probe can surround, but not contact directly, the solution sample. In some embodiment, the NMR probe can contain the solution sample therein. In some embodiments, the NMR probe can be configured to be surrounded by the sample to be measured. In another embodiment, the NMR probe can be configured to be located a distance away from the sample to be measured.

Figure 2:
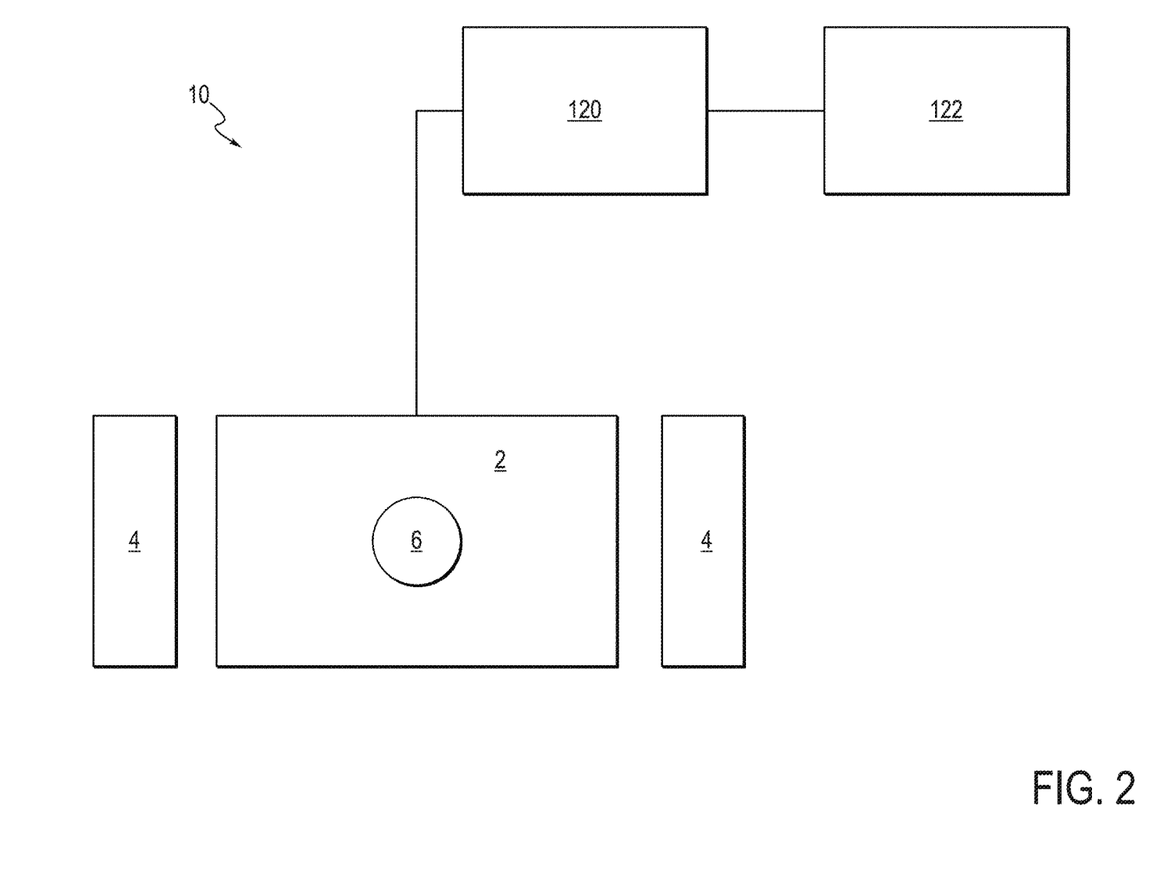
FIG. 2 is a simplified diagram illustrating a system for testing samples in a laboratory setting according to one exemplary embodiment.

In one embodiment, a test apparatus 10 as shown in FIG. 2 is used to conduct the NMR measurements. In the embodiment shown, a test sample 6 is physically placed within the NMR probe 2. The NMR probe 2 includes the RF coils and associated electronics. The NMR probe 2 is surrounded by permanent magnets 4 which provide the magnetic field. The NMR probe 2 is connected to a console 120 which includes controls for operating the NMR probe 2. The console in turn is connected to a computer processor 122 for processing the data received from the NMR probe 2.

Figure 3:
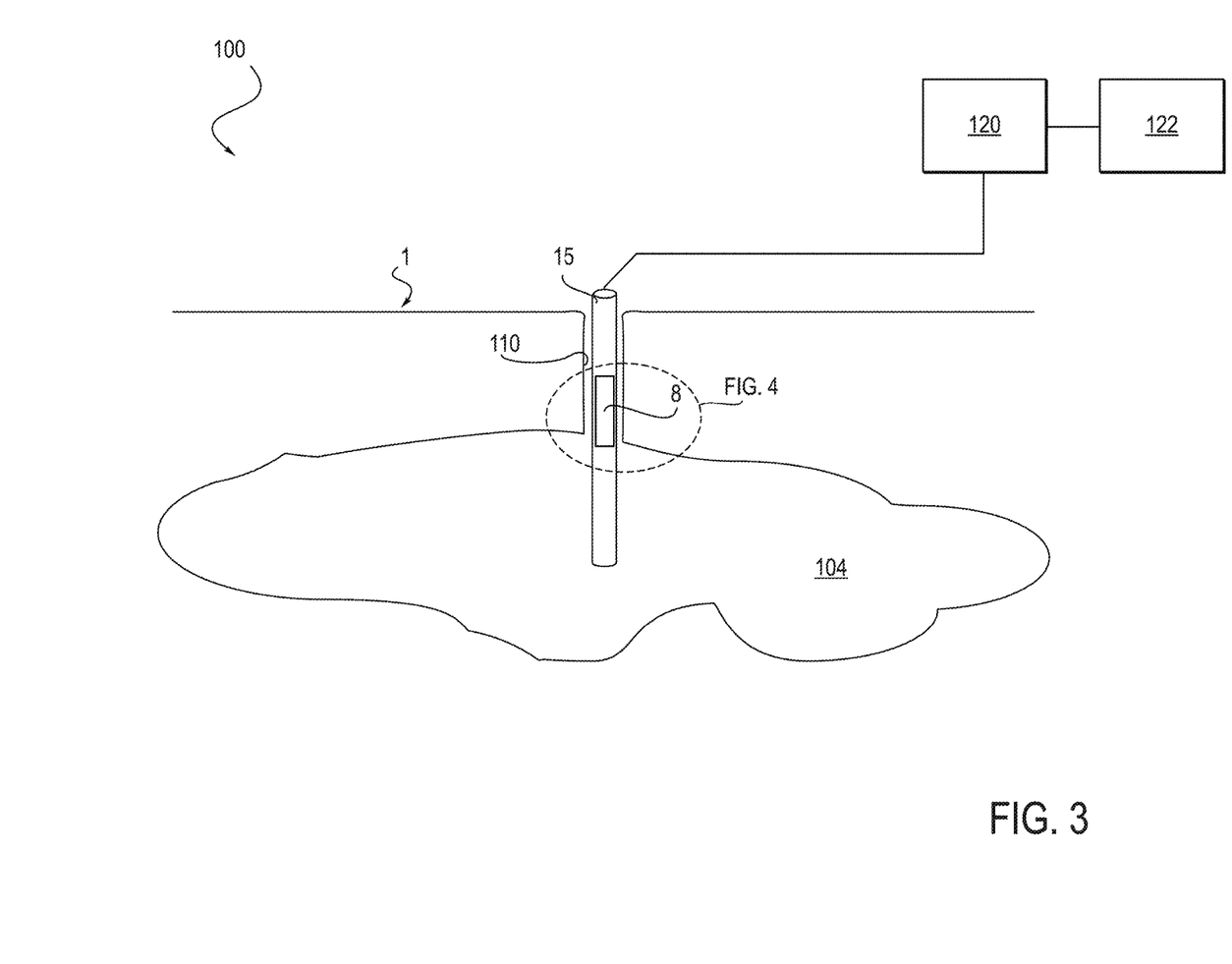
FIG. 3 is a schematic of a system including at least one subterranean reservoir from which hydrocarbons are produced in which asphaltene concentration is determined according to one embodiment.

In some embodiments, such as that illustrated in the system 100 FIG. 3, a test apparatus 8 is incorporated into a downhole logging tool 15. The downhole logging tool 15 can be inserted in a hole (or conduit) 110 leading to a hydrocarbon producing reservoir 104. The hydrocarbon producing reservoir 104 is a formation below the surface of the earth 1. Thus the test apparatus 8 can be located downhole in a hydrocarbon producing reservoir 104 or in the vicinity of the hydrocarbon producing reservoir. The logging tool 15 is connected to a console 120 which in turn is connected to a computer processor 122 located topsides.

Figure 4:
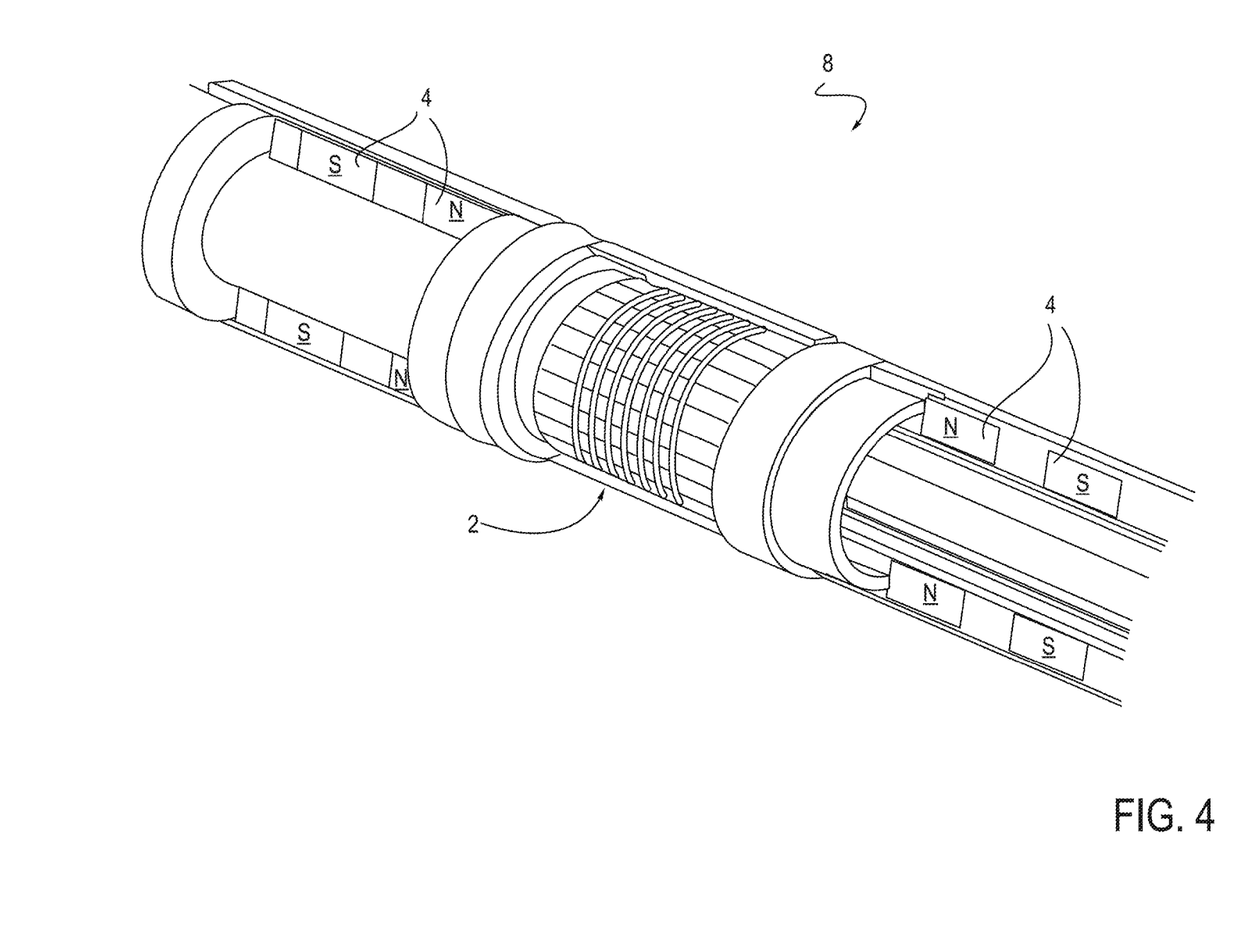
FIG. 4 is a simplified diagram illustrating an apparatus for testing samples downhole in a subterranean reservoir according to another exemplary embodiment.

As shown in FIG. 4, the test apparatus 8 includes one or more NMR probes 2 and associated electronics for transmitting and receiving RF signals and permanent magnets 4 for creating a magnetic field. The test apparatus 8 is incorporated in downhole logging tool 15 which can optionally include other measurement devices and sensors. The downhole logging tool 15 can be passed through a hole (or conduit) 110 drilled in the earth 1 into formation 104. The sample being measured surrounds the test apparatus 8. The sample may be within a few inches of the test apparatus 8, e.g., 2-3 inches, or more, depending on the sensitivity of the probe 2 within the test apparatus 8.

In some embodiments, the NMR probe is located at the surface. In such cases, one or more surface coils and/or antennae can be used to emit RF pulses to make NMR measurements of subsurface hydrocarbons.

The processor 122 is capable of receiving signals indicative of the diffusivity and T2 determined for a given solution sample. The processor 122 is capable of calculating the ratio of diffusivity to T2 for the given solution sample. The processor is further capable of accessing the linear equation, also referred to as the model, and solving the linear equation using the ratio of diffusivity to T2 for the given solution sample to determine the asphaltene concentration in the given solution sample.

EXAMPLES

Experiments were performed on two different types of samples, crude oils with different asphaltene contents and toluene with different asphaltene contents. The experimental samples were prepared as follows.

For the crude oil samples, dry asphaltenes were extracted from two crude oils, referred to as A Crude Oil A and Crude Oil B, using hot heptane filtration. The crude oil samples were dispersed in n-heptane at 60° C. and filtered through a glass-fiber pad. The insoluble material was washed, dried and weighed.

The dry asphaltenes extracted from Crude Oil A were gradually added to Crude Oil A to achieve different asphaltene concentrations. Likewise, the dry asphaltenes extracted from Crude Oil B were gradually added to Crude Oil B to achieve different asphaltene concentrations. The dissolution of the dry asphaltenes in the crude oils was facilitated by an ultrasonic bath (AmericanBrand™, available from American Scientific Products, McGaw Park, Ill.). The weight of crude oil and added asphaltenes were recorded. The asphaltene content was calculated based on weight. In addition to Crude Oil A and Crude Oil B, eight other crude oil samples from different locations around the world with different original asphaltene concentrations were employed for D and T2 NMR measurements, for a total of 10 samples. Crude Oil A was prepared in four different concentrations, i.e., the original concentration and three higher concentrations of asphaltene. Crude Oil B was prepared in two different concentrations, i.e., the original concentration and one higher concentration. The remaining eight different crude oils were prepared with their original concentrations.

For the toluene solutions, different amounts of dry asphaltenes extracted from Crude Oil B were added to 100% toluene to generate a series of toluene-asphaltene solutions that covered a wide range of asphaltene concentrations. Again, the dissolution of the dry asphaltenes in the toluene was facilitated by an ultrasonic bath. Samples with eight different concentrations were prepared.

Figure 1:
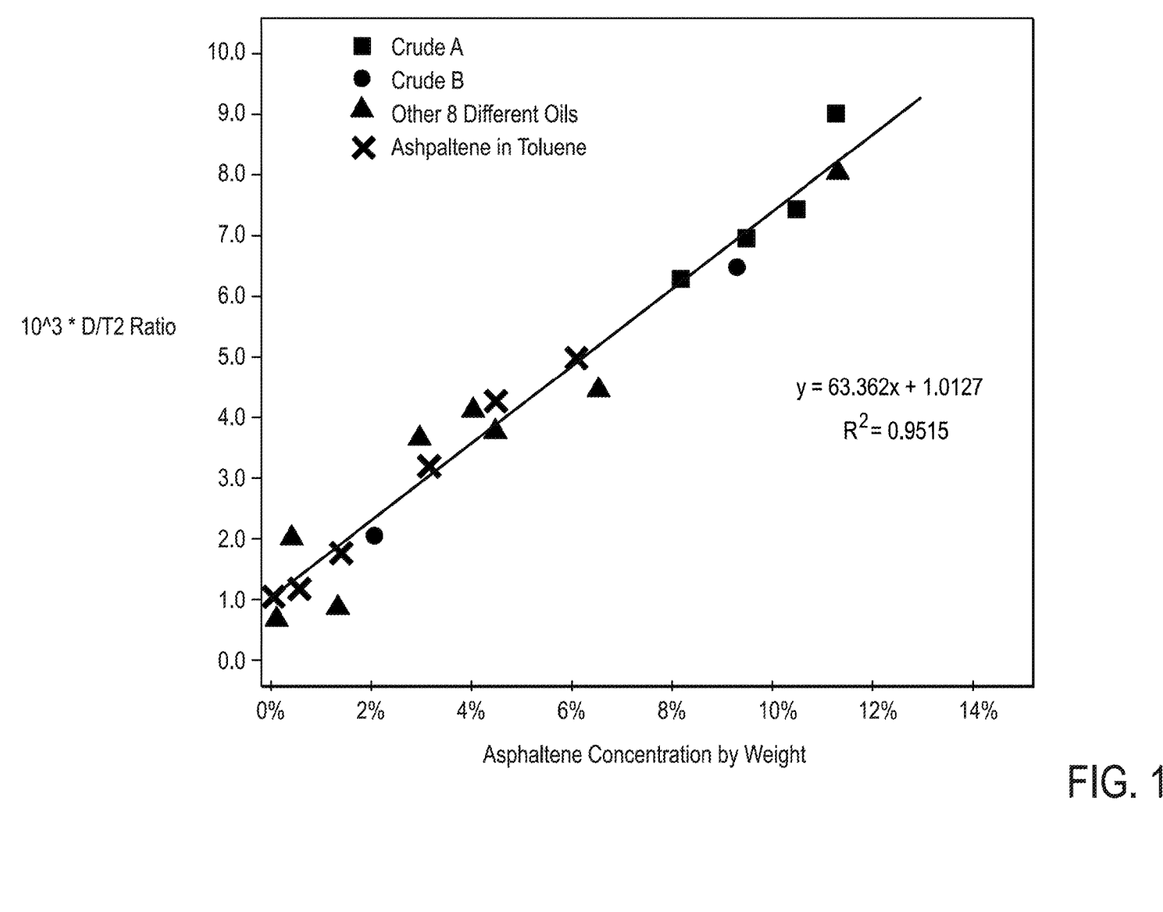
FIG. 1 is a graph correlating the ratio of diffusivity to relaxation time to the asphaltene concentration by weight in crude oil and toluene solutions according to one exemplary embodiment.

D and T2 NMR measurements were performed on each crude oil-asphaltene and toluene-asphaltene sample. The NMR spectrometer console was obtained from Oxford Instruments plc (Abingdon, England), model Maran® Ultra. The operating software for the NMR spectrometer was RINMR, Version 5.3.0.0 available from Oxford Instruments plc. The NMR spectrometer was operated at a frequency of 6.017 MHz. A D-T2 two-dimensional sequence was applied to obtain diffusivity (D) and transverse relaxation time (T2) of the target sample simultaneously. The NMR probe was located surrounding but not contacting the target samples. The obtained D and T2 NMR data for the crude oils and toluene solutions were organized in the form of D/T2 Ratio vs. Asphaltene Concentration by Weight as shown in FIG. 1. The plot in FIG. 1 is a graph of $D/T2 \times 10^3$ by percentage asphaltene concentration by weight. A linear relationship is observed, and a linear equation was fit to the linear relationship. As shown on the plot, the linear equation is:

$$y=63.362x+1.0127$$

This linear equation can be solved for an additional sample to determine the asphaltene concentration once D and T2 have been measured for the sample.

Advantageously, in one embodiment, a model is provided of the correlation between D/T2 ratio and asphaltene content in either crude oils or toluene solvent. Using the model, asphaltene content can be determined with high accuracy ($R^2>0.95$). In one embodiment, the correlation can be incorporated in 2D NMR logging technology for in-situ quantitative evaluation of asphaltene content in hydrocarbon producing formations. In one embodiment, the correlation can be incorporated in Downhole Fluid Analysis (DFA) technology for quantitative analysis of asphaltene in reservoir fluids at downhole conditions. DFA technology combines a set of tools having different functions that can be applied downhole.

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

It should be noted that only the components relevant to the disclosure are shown in the figures, and that many other components normally part of a two-dimensional NMR measurement system are not shown for simplicity.

Unless otherwise specified, the recitation of a genus of elements, materials or other components, from which an individual component or mixture of components can be selected, is intended to include all possible sub-generic combinations of the listed components and mixtures thereof. Also, "comprise," "include" and its variants, are intended to be non-limiting, such that recitation of items in a list is not to the exclusion of other like items that may also be useful in the materials, compositions, methods and systems of this invention.

From the above description, those skilled in the art will perceive improvements, changes and modifications, which are intended to be covered by the appended claims.

What is claimed is:

1. A method for determining a concentration of asphaltenes in a solution, comprising:
   a. establishing a model for estimating the concentration of the asphaltenes in the solution, comprising the steps of:
      i. preparing a plurality of samples of solutions of the asphaltenes in a solvent wherein the solutions have varying concentrations of the asphaltenes and wherein concentrations of the asphaltenes are known for each sample within the plurality of samples;
      ii. exciting and detecting NMR signals from each sample within the plurality of samples using a two-dimensional NMR spectrometer;
      iii. measuring a diffusivity of an at least one response signal that is an NMR signal from the two-dimensional NMR spectrometer corresponding to each sample within the plurality of samples;
      iv. measuring a relaxation time of the at least one response signal that is the NMR signal from the two-dimensional NMR spectrometer corresponding to each sample within the plurality of samples;
      v. calculating a ratio of the diffusivity to the relaxation time for each sample within the plurality of samples;
      vi. fitting a linear equation to describe a relationship between the ratio of the diffusivity to the relaxation time and an asphaltene concentration by weight for each sample within the plurality of samples; and
   b. measuring the diffusivity and the relaxation time of the at least one response signal that is the NMR signal from the two-dimensional NMR spectrometer corresponding to a given solution sample for which the concentration of the asphaltenes is desired to be determined;
   c. calculating the ratio of the diffusivity to the relaxation time for the given solution sample;
   d. solving the linear equation as determined in step (a) (vi) using the ratio of the diffusivity to the relaxation time for the given solution sample as determined in step (c) to determine the asphaltene concentration in the given solution sample.

2. The method of claim 1, wherein the solvent comprises toluene.

3. The method of claim 1, wherein the diffusivity and the relaxation time measured in step (b) are received from an NMR probe located downhole in a hydrocarbon producing reservoir.

4. A system, comprising:
   a. an NMR probe located proximate a fluid solution for determining a diffusivity and a relaxation time of the fluid solution using exciting and detecting NMR signals from each sample in a two-dimensional NMR spectrometer;
   b. a computer processor that performs:
      i. receiving the diffusivity and the relaxation time of the fluid solution from the NMR probe;
      ii. calculating a ratio of the diffusivity to the relaxation time for the fluid solution;
      iii. accessing a linear equation describing a relationship between the ratio of the diffusivity to the relaxation time and an asphaltene concentration by weight; and
      iv. solving the linear equation to determine the asphaltene concentration by weight in the fluid solution based on the ratio of the diffusivity to the relaxation time for the fluid solution.

5. The system of claim 4, wherein the NMR probe is located downhole in a hydrocarbon producing reservoir.

6. The method of claim 1, where the asphaltene concentration that is determined in step (d) is determined by weight with an accuracy of $R^2>0.95$.

7. The method of claim 1, wherein the diffusivity and the relaxation time of the given solution sample are obtained simultaneously in step (b) using a D-T2 two-dimensional sequence.

8. The method of claim 1, wherein the relaxation time is a transverse relaxation time.

9. The method of claim 1, wherein the solvent is an extracted crude oil, wherein the asphaltenes were removed by a hot heptane filtration.

10. The system of claim 4, wherein the NMR probe is configured to be surrounded by the fluid solution.

11. The system of claim 4, wherein the NMR probe contains the fluid solution therein.

12. The method of claim 1, wherein the two-dimensional NMR spectrometer is a low-frequency two-dimensional NMR spectrometer.

13. The method of claim 12, additionally comprising performing a data inversion with a multidimensional inverse Laplace transformation.

14. The system of claim 4, wherein the two-dimensional NMR spectrometer is a low-frequency two-dimensional NMR spectrometer.

\* \* \* \* \*